United States Patent
Mialhe

(10) Patent No.: US 7,753,925 B2
(45) Date of Patent: Jul. 13, 2010

(54) OCCLUSIVE DEVICE FOR MEDICAL OR SURGICAL USE

(76) Inventor: Claude Mialhe, 292 Chemin de la Direne, Draguignan (FR) F-83300

( * ) Notice: Subject to any disclaimer, the term of this patent is extended or adjusted under 35 U.S.C. 154(b) by 962 days.

(21) Appl. No.: 10/535,173

(22) PCT Filed: Oct. 15, 2003

(86) PCT No.: PCT/FR03/50092

§ 371 (c)(1),
(2), (4) Date: May 16, 2005

(87) PCT Pub. No.: WO2004/045418

PCT Pub. Date: Jun. 3, 2004

(65) Prior Publication Data

US 2006/0058820 A1 Mar. 16, 2006

(30) Foreign Application Priority Data

Nov. 15, 2002 (FR) .................................. 02 14287

(51) Int. Cl.
*A61B 17/08* (2006.01)
(52) U.S. Cl. .................... 606/158; 623/1.13; 623/1.15; 623/1.16; 623/1.24; 623/1.25
(58) Field of Classification Search ............... 606/157, 606/158, 200, 191, 213, 153; 600/235; 604/8, 604/9; 623/1.13, 1.15, 1.16, 1.24–1.25
See application file for complete search history.

(56) References Cited

U.S. PATENT DOCUMENTS

| | | | | |
|---|---|---|---|---|
| 3,874,388 A | * | 4/1975 | King et al. ................ 606/232 |
| 4,580,573 A | * | 4/1986 | Quinn ........................ 600/434 |
| 4,969,896 A | * | 11/1990 | Shors ........................ 623/1.44 |
| 5,084,065 A | * | 1/1992 | Weldon et al. ............. 623/1.44 |
| 5,441,515 A | * | 8/1995 | Khosravi et al. ........... 606/194 |
| 5,449,368 A | * | 9/1995 | Kuzmak ..................... 606/157 |
| 5,522,822 A | * | 6/1996 | Phelps et al. ............... 606/151 |
| 5,562,728 A | * | 10/1996 | Lazarus et al. ............. 623/1.14 |
| 5,603,722 A | * | 2/1997 | Phan et al. ................. 623/1.18 |
| 5,665,117 A | * | 9/1997 | Rhodes ....................... 623/1.1 |
| 5,693,088 A | * | 12/1997 | Lazarus ..................... 623/1.35 |
| 5,709,713 A | * | 1/1998 | Evans et al. ............... 623/1.53 |
| 5,723,003 A | * | 3/1998 | Winston et al. ............ 623/1.13 |
| 5,725,552 A | * | 3/1998 | Kotula et al. .............. 606/213 |
| 5,843,160 A | * | 12/1998 | Rhodes ...................... 623/1.35 |
| 5,860,998 A | * | 1/1999 | Robinson et al. ........... 606/194 |
| 5,861,003 A | * | 1/1999 | Latson et al. .............. 606/213 |
| 5,957,913 A | * | 9/1999 | de la Torre et al. ............. 606/1 |

(Continued)

FOREIGN PATENT DOCUMENTS

EP 0 834 279 4/1998

(Continued)

*Primary Examiner*—(Jackie) Tan-Uyen T Ho
*Assistant Examiner*—Son Dang
(74) *Attorney, Agent, or Firm*—Young & Thompson

(57) ABSTRACT

An occlusive device includes a hollow cylindrical element which can be twisted axially in order to create a constricted region. The device also includes a body which can be deformed by transverse compression and which is applied against the inner wall of the aforementioned cylindrical element, the body having a through hole along the axis of the cylindrical element.

15 Claims, 3 Drawing Sheets

U.S. PATENT DOCUMENTS

| | | | |
|---|---|---|---|
| 6,042,605 A * | 3/2000 | Martin et al. | 623/1.13 |
| 6,096,052 A * | 8/2000 | Callister et al. | 606/157 |
| 6,124,523 A * | 9/2000 | Banas et al. | 623/1.15 |
| 6,168,619 B1 * | 1/2001 | Dinh et al. | 623/1.13 |
| 6,355,061 B1 * | 3/2002 | Quiachon et al. | 623/1.36 |
| 6,425,916 B1 * | 7/2002 | Garrison et al. | 623/2.11 |
| 6,432,116 B1 * | 8/2002 | Callister et al. | 606/157 |
| 6,579,314 B1 * | 6/2003 | Lombardi et al. | 623/1.44 |
| 7,008,439 B1 * | 3/2006 | Janzen et al. | 606/213 |
| 2001/0037053 A1 * | 11/2001 | Bonadio et al. | 600/208 |
| 2002/0029051 A1 * | 3/2002 | Callister et al. | 606/157 |
| 2002/0032481 A1 * | 3/2002 | Gabbay | 623/2.11 |
| 2002/0151958 A1 * | 10/2002 | Chuter | 623/1.13 |
| 2003/0040772 A1 * | 2/2003 | Hyodoh et al. | 606/200 |
| 2003/0109893 A1 * | 6/2003 | Vargas et al. | 606/153 |
| 2003/0139802 A1 * | 7/2003 | Wulfman et al. | 623/1.15 |
| 2003/0144725 A1 * | 7/2003 | Lombardi | 623/1.13 |
| 2003/0158578 A1 * | 8/2003 | Pantages et al. | 606/213 |
| 2003/0225447 A1 * | 12/2003 | Majercak et al. | 623/1.13 |
| 2003/0229366 A1 * | 12/2003 | Reggie et al. | 606/158 |
| 2004/0019374 A1 * | 1/2004 | Hojeibane et al. | 623/1.13 |
| 2004/0215333 A1 * | 10/2004 | Duran et al. | 623/1.24 |
| 2005/0096735 A1 * | 5/2005 | Hojeibane et al. | 623/1.24 |
| 2007/0185518 A1 * | 8/2007 | Hassier, Jr. | 606/190 |

FOREIGN PATENT DOCUMENTS

| | | |
|---|---|---|
| WO | WO 02/19926 | 3/2002 |
| WO | WO 02/32320 | 4/2002 |

* cited by examiner

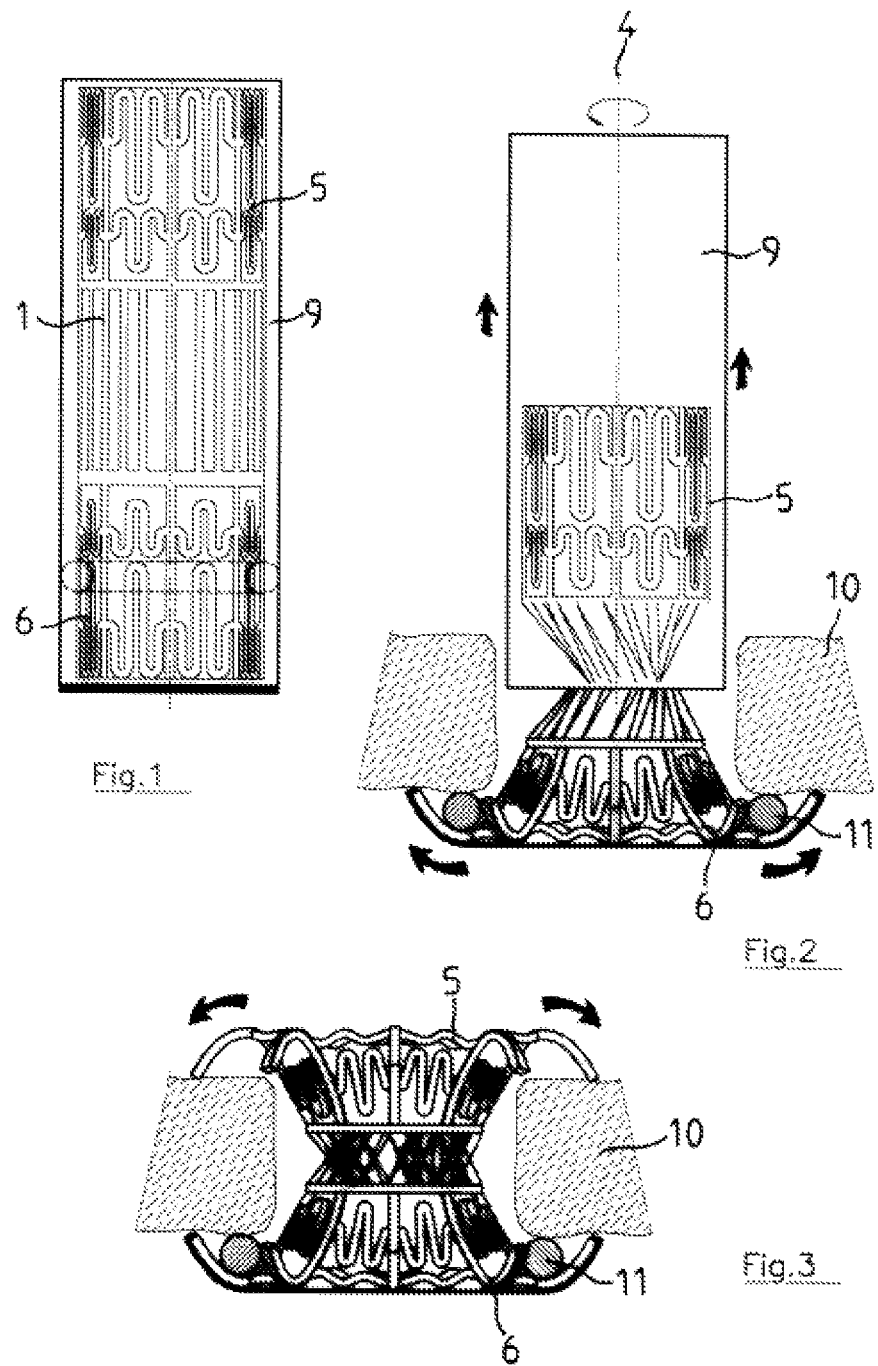

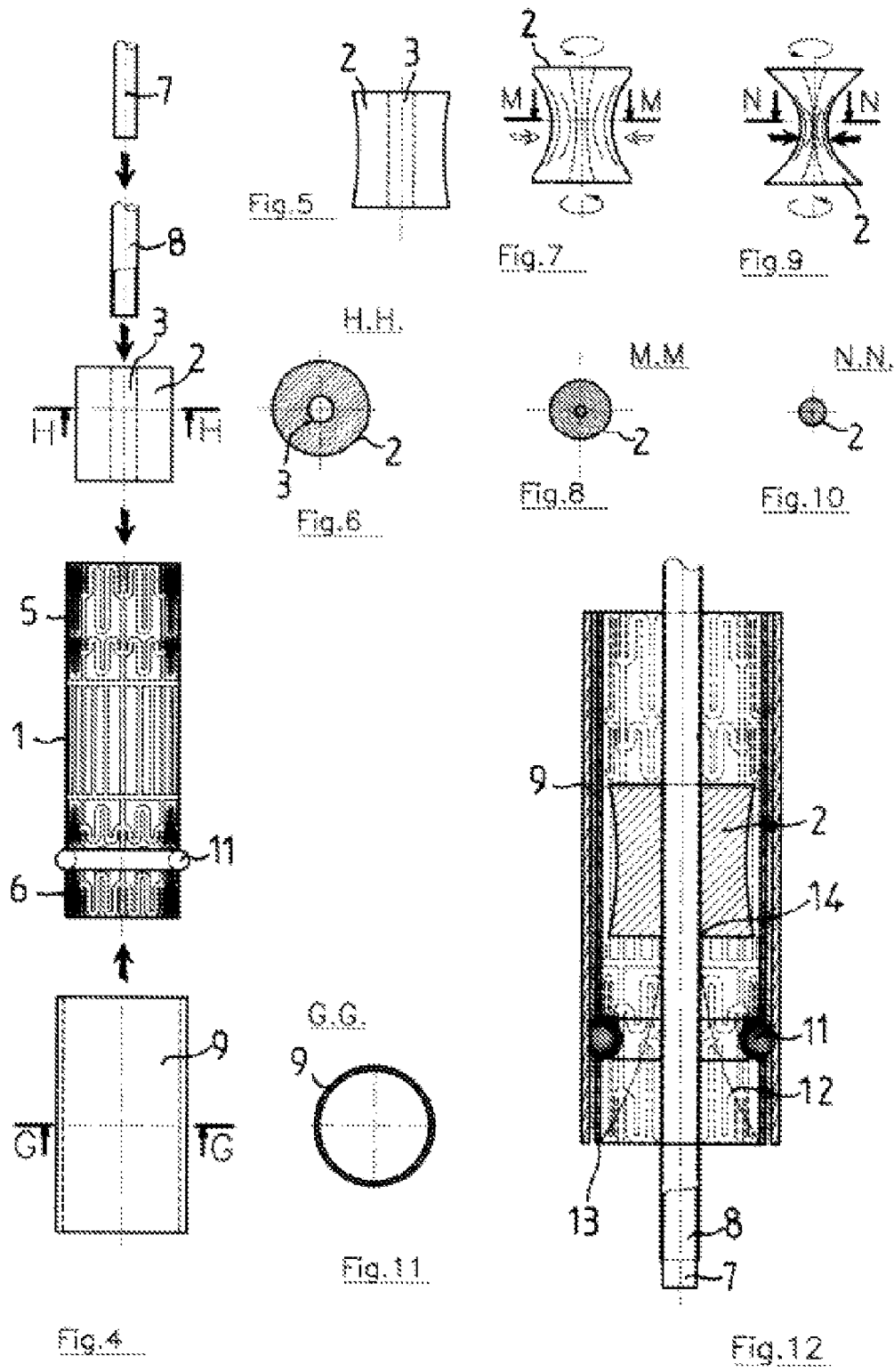

OCCLUSIVE DEVICE FOR MEDICAL OR SURGICAL USE

The present invention relates to an occlusive device for medical or surgical use, and to a vascular occlusion device and a valve for surgical or medical instruments.

The invention will find applications, in particular, in the manufacture and use of occlusive prostheses for all types of vessels in humans or animals, prostheses that may also include transparietal and endovascular devices.

The invention also relates to the field of surgical or medical instruments and in particular introducer type instruments that may be used during endovascular surgery, including percutaneous and/or transparietal operations, which require the presence of obturation elements able to ensure that the introducer is sealed.

The quality of the occlusion is a constant problem according to the current state of the art, both in the field of vascular prostheses and for the creation of valves.

Document WO-A-0219926 relates to a vascular occlusion device comprised of two expanding elements for attachment by support against two portions of the vessel's wall, along with an intermediate section that can be twisted to an adjustable degree according to the relative position of the two expanding elements. A maximum striction area is thus created, defining the degree of occlusion.

According to this document, total or partial obturation is achieved by means of the twisting deformation of an element.

This technique provides a great ease of intervention and the ability to fine tine the degree of obturation.

There is, however, a need to further improve the sealing provided by this type of device.

The present invention provides a solution to this by appended a second occlusion element that acts in collaboration with the twist deformable element.

In a preferred embodiment, the invention also possesses the advantage of offering additional tightness means in the form of seals that can be applied to the wall of a vessel.

Still advantageously, for the creation of a vascular occlusion device, the invention allows both the constitution of an element able to provide obturation and guiding through cooperation with a removable guide present in the device during the procedure.

Other purposes and advantages shall appear during the following description of a preferred embodiment of the invention, which is nevertheless not limiting.

The present invention relates to an occlusive device for medical or surgical use comprising a hollow cylindrical element that can be twisted along its axis to create a striction zone. It comprises a transverse compression deformable body, applied to the inner wall of the cylindrical element and possessing a opening oriented according to the axis of the cylindrical element.

According to preferred variants, this device is such that:
 The deformable body is attached to the inner wall of the cylindrical element,
 The deformable body is made from a polymer material,
 there are two end parts, surrounding the cylindrical element and whose angular position determines the torsion of said cylindrical element.
 The cylindrical element and the deformable body both have circular cross sections.

The invention also relates to a vascular occlusion device comprising an occlusive device according to the invention.

This vascular occlusion device is advantageously embodied with the following additional properties:

Two end parts, surrounding the cylindrical element and whose relative angular position determines the torsion of said cylindrical element, said end parts possessing means of attachment to the wall of a vessel,
 The attachment means are expanding elements,
 It possesses a seal on the outer surface of at least one of the expanding elements, said seal being appropriate for application to the wall of a vessel,
 It presents a peripheral obturation web extending from one end of the deformable body to the edge of the corresponding expanding element,
 It possesses a removable guide oriented according to the axis of the cylindrical element and crossing the opening of the deformable body.
 It possesses a removable sheath inserted between the wall of the opening in the deformable body and the outer wall of the guide,
 It comprises a removable sleeve surrounding the occlusive device, The invention also relates to a valve for surgical or medical instruments comprising a closeable passage and characterised by the fact that it comprises an occlusive device according to the invention.

In a preferred embodiment, this valve is such that the cylindrical element can be twisted by means of two rings, each integral to one end of the cylindrical element.

The appended drawings are given as an example and do not limit the invention. They represent only one embodiment of the invention and allow it to be easily understood.

FIG. 1 is a general view of the device concerned by the invention for a vascular occlusion application.

FIG. 2 illustrates a step in the transparietal implementation of a vascular occlusion device.

FIG. 3 shows an example of the end result of transparietal occlusion.

FIG. 4 is an exploded view of the different elements making up the occlusive device according to the invention in a preferred embodiment.

FIG. 5 is a side view of the deformable body and

FIG. 6 is a section.

FIG. 7 is a side view of the deformable body as it is being deformed and

FIG. 8 is a section of this same situation.

FIG. 9 is a side view of the deformable body at the end of deformation and

FIG. 10 is a section of this same situation.

FIG. 11 illustrates a section of a sheath used for a vascular occlusion device.

Figure 13:
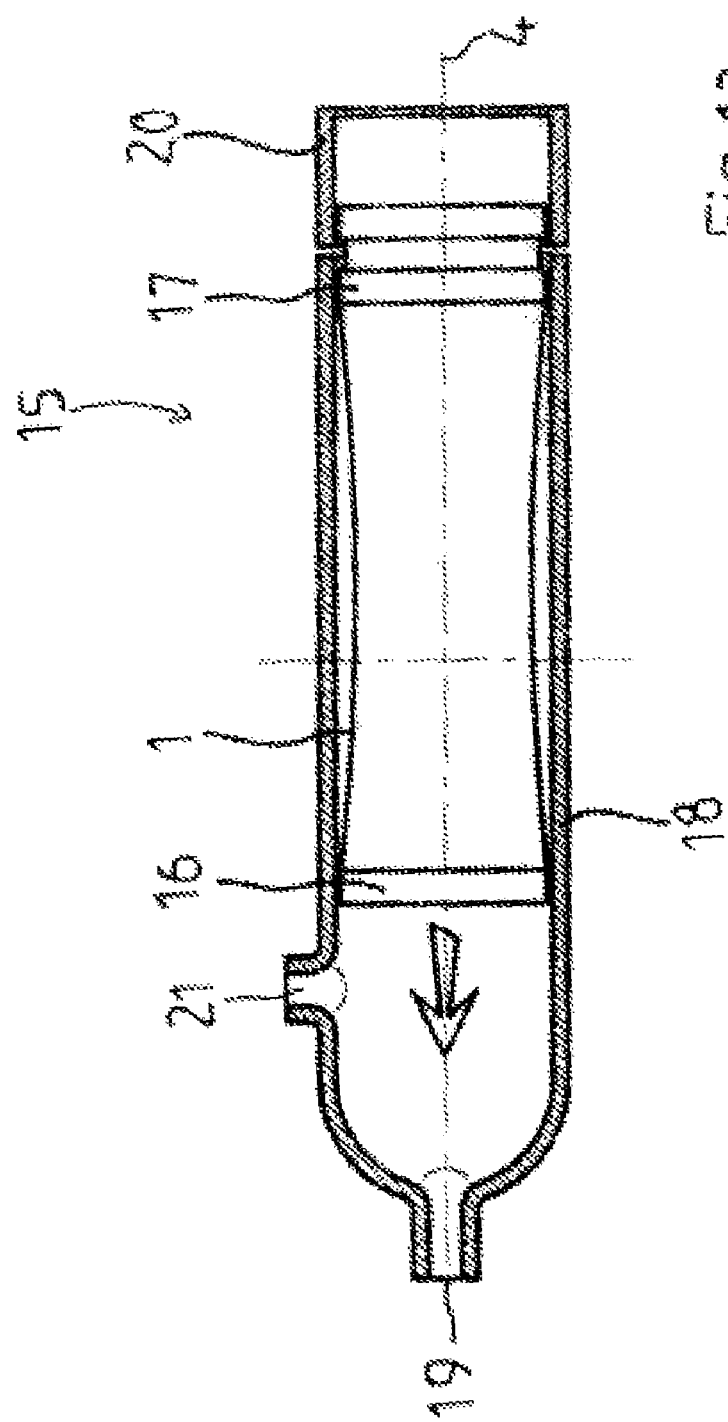

FIG. 12 presents a longitudinal section of a vascular occlusion device.

FIG. 13 shows an example of insertion of an occlusive device according to the invention in an introducer valve.

The occlusive device according to the invention can be used in various medical or surgical fields. The remainder of the description shall outline more specifically an embodiment applying the occlusive device to the creation of a vascular occlusion device, along with an embodiment of the invention applying the occlusive device to valves for surgical or medical instruments.

In general terms, the occlusive device comprises a hollow cylindrical element that can be twisted according to its axis, this deformation creating a striction zone advantageously widest towards the middle of the length of the hollow cylindrical element 1, although this is not limiting.

The cylindrical element can be twisted by modifying the relative angular positions of its ends.

Furthermore, the occlusive device comprises a transverse compression deformable body 2, show more precisely in FIGS. 4 to 10. This body 2 possesses a shape and dimensions adapted to its application to the inner wall of the cylindrical element 1.

In a preferred embodiment, the deformable body 2 is furthermore attached to said inner wall of the cylindrical element 1 in such a manner as to follow this latter's deformation.

The body 2 further comprises a through hole 3 along the axis 4 of the cylindrical element 1.

The hole 3 offers a residual passage that can be closed to achieve obturation. In open position, the hole 3 allows the passage of fluid or solid elements such as long objects in the case of an application to valves for introducer type surgical instruments. Concerning application to the vascular occlusion device, the hole 3 is used to receive a guide 7 that can be used when manipulating the occlusion device during the surgical procedure.

Different materials can be used for constructing the body 2, and in particular a polymer material, presenting, or not, shape memory properties. Other materials that can undergo transverse compression deformation during torsion of the hollow cylindrical element 1 may be used.

Still in a preferable manner and in reference to the drawings, the invention's occlusive device possesses a hollow circular cross section, in particular concerning the cylindrical element 1 and the deformable body 2.

The following describes in a more precise manner an embodiment of the occlusive device for a vascular occlusion device application.

In this context, reference is made to FIGS. 1 to 12, presenting a specific embodiment of this application.

FIG. 1 shows in detail an example of structure that the cylindrical element 1 can present. In particular, element 1 may be in the form of a metallic frame, Nitinol® based for example and presenting three distinct zones. The first zone, central, constitutes the cylindrical element 1 itself and can be twisted as shown in FIGS. 2 and 3. Around the cylindrical element 1, two expanding elements 5 in the form of self-expanding frames, are represented and may be in a configuration as shown in the field of endovascular prostheses. Expanding elements 5 and 6 possess shape memory properties allowing them to undergo deployment deformation when released.

This release occurs through a sleeve 9 that surrounds the whole device prior to implementation by the practitioner. The cylindrical element 1 and expanding elements 5 and 6 are held within the sleeve 9 in resting position.

During implantation, the practitioner progressively removes the sleeve 9 in such a manner as to release an initial expanding element to apply it against the wall of a vessel 10.

This removal can be achieved using a push element in the form of a long, hollow cylindrical element appropriate, by virtue of its width, to be applied to the edge of the occlusive device to exercise a force contrary to removal of the sleeve 9, thus immobilising the occlusive device during removal.

At this time, the vascular occlusion device is partially positioned, but expanding element 5 is still in the sleeve 9. Rotation of the sleeve 9 by the practitioner twists cylindrical element 1, thus creating a striction zone, as represented in FIG. 2.

When the desired degree of striction is achieved (this can be easily adjusted by means of the amplitude of rotation implemented by the practitioner), the other expanding element 5 is released from the sleeve 9 by sliding it out (again using a push device if necessary). This release deploys the expanding element and applies it to the vessel wall 10.

FIGS. 2 and 3 more specifically show a transparietal application of the present vascular occlusion device. In this context, it is expanding element 6 that is applied to the internal wall and expanding element 5 to the outer wall.

FIG. 4 provides a more detailed view of cooperation between the various constitutive elements of the vascular occlusion device.

In this context, the sheath 9 receives, in its inner volume, the assembly comprised of the cylindrical element 1 and the expanding elements 5 and 6. The cylindrical element 1 further receives, in its inner volume, for application onto its inner wall, a deformable body 2 with a through hole 3 along the device's axis.

The through hole 3 is itself able to receive a guide 7 during manipulations. In a preferred embodiment, a sheath 8 is inserted between the inner wall of the through hole 3 and the outer surface of the guide 7. The sheath 8, made for example from a metallic material, prevents any deterioration of the body 2 during guide 7 movements and confers rigidity on the assembly. The guide 7 and the sheath 8 are designed to be removable in such a manner as to be removed by the practitioner during the operation, prior to twisting.

The combination of these constituents is more specifically represented in FIG. 12 according to a preferred embodiment.

FIGS. 5 to 10 display various states of mechanical stress of the deformable body 2. In this context, FIGS. 5 and 6 respectively illustrate side and cross section views of the resting body 2. The through hole 3 is perfectly free.

During twisting of the cylindrical element 1, the body 2 is compressed according to the direction of the arrows shown in FIG. 7. The through hole 3 is then deformed, thus reducing its diameter as displayed in FIG. 8. This leads to obturation, which may be total or partial.

By further emphasizing the torsion stress applied to the cylindrical element 1, the transverse compression of the body 2 is increased until complete obturation of the holes 2 is achieved. This situation is represented in FIGS. 9 and 10.

Preferably, the seal achieved by means of the occlusive device integrated into the vascular occlusion device should be supported by additional means.

More specifically, a seal 11, applied to the external periphery of one of the expanding elements 6 may be used. An O ring seal, for example, may be used, made from a sufficiently deformable material to follow the deformation of element 6 during its deployment.

The seal 11 is applied, through this deployment, to the wall of the vessel 10.

Still in a complementary manner to an occlusive device, the vascular occlusion device may include a web 12, as shown in FIG. 12. In its resting position, the web 12 possesses a roughly tapered circular shape, possibly slightly bent, extending from one end 14 of the obturation element and the edge 13 of the expanding element 6 located on the same side. By establishing such a continuous web 12, a "funnel" effect is generated, thus avoiding any blood leakages out of the zone delimited by the through hole 3.

When deploying the expanding element 6, the web 12 follows the corolla deformation.

Below we describe more specifically a second embodiment of the occlusive device of the invention for an application to valves for surgical and medical instruments.

In particular, FIG. 13 illustrates the formation of such a valve 15 that can be integrated into or added to a body introduction instrument.

For this purpose, the valve 15 comprises a shell 18 able to receive, in its inner volume, an occlusive device comprising a cylindrical element 1.

The valve 15 furthermore comprises a proximal end with an opening 19 for passing elements during introduction, along with an additional opening 21.

The distal end 20 of the valve 15 is able to receive an additional valve element or a simple angular control element.

According to this application, the cylindrical element 1 is surrounded by rings 16 and 17, whose relative angular position can be adjusted in such a manner as to ensure the twisting of element 1.

Though not represented, element 1 receives, in its inner volume, a deformable body 2.

According to the example, rotation of ring 17, caused by manipulating the distal end 20 of valve 15, alters the relative angular position of rings 16 and 17 and causes twisting of element 1. This twisting deformation causes a transverse compression of the body 2 due to the resulting striction.

It is thus possible to totally or partially open or close through hole 3 by altering the position of ring 17, and this while ring 16 is fixed.

Of course, this embodiment is only an example and other variants may be considered.

In particular, ring 16 may be free to rotate, while ring 17 could be fixed. Furthermore, the rings 16 and 17 may additionally be moved together or apart, for example by means of a helicoidal runner type link between the housing 18 of the valve 15 and the ring 17.

In the context of this application, the cylindrical element 1 comprises a sealed wall and may be made, in particular, from a woven (or not) textile material, or from a polymeric material such as P.T.F.E. (Poly Tetra Fluoro Ethylene).

REFERENCES

1. Cylindrical element
2. Deformable body
3. Hole
4. Axis
5. Expanding element
6. Expanding element
7. Guide
8. Sheath
9. Sleeve
10. Vessel wall
11. Seal
12. Web
13. Edge
14. End of body
15. Valve
16. Ring
17. Ring
18. Housing
19. Opening
20. Distal end
21. Opening

The invention claimed is:

1. A vascular occlusion device comprising:
an occlusive device having a hollow cylindrical element (1) that twisted to its axis to create a striction zone, comprising:
a transverse compression deformable body (2) applied to the inner wall of the cylindrical element (1),
comprising a through hole (3) according to axis (4) of the cylindrical element (1), and
the device further comprising two end parts, surrounding the cylindrical element (1) and whose relative angular position determines the torsion of the cylindrical element (1), said end parts possessing means of attachment to the wall of a vessel,
the attachment means are expanding elements (5 and 6),
wherein the deformable body (2) and the cylindrical element (1) are distinct parts, and
the deformable body has a thickness greater than the thickness of the cylindrical element.

2. The device according to claim 1, wherein the deformable body (2) is attached to the inner wall of the cylindrical element (1).

3. The device according to claim 1, wherein the deformable body (2) is made from a polymer material.

4. The device according to claim 1, wherein the cylindrical element (1) and the deformable body (2) both have circular cross sections.

5. The device according to claim 1, comprising a seal (11) on the outer surface of at least one of the expanding elements (5 and 6), said seal (11) being appropriate for application to the wall of a vessel.

6. The device according to claim 1, comprising a peripheral obturation web (12) extending from one end of the deformable (2) body (14) and the edge (13) of the expanding element (5, 6).

7. The device according to claim 1, comprising a removable guide (7) positioned according to the axis (4) of the cylindrical element (1) and crossing the hole (3) in the deformable body (2).

8. The device according to claim 7, comprising a removable sheath (8) inserted between the wall of the hole (3) in the deformable body (2) and the outer wall of the guide (7).

9. The device according to claim 1, comprising a removable sleeve (9) surrounding the occlusive device.

10. The device according to claim 3, wherein the polymer material has shape memory properties.

11. The device according to claim 1, wherein the expanding elements are self-expanding frames.

12. The device according to claim 1, further comprising a Nitinol® based metallic frame having a first central zone constituting the cylindrical element and two zones around the first zone, said two zones constituting expanding elements.

13. The vascular occlusion device according to claims 1, wherein the cylindrical element comprises a sealed wall.

14. The vascular occlusion device according to claims 1, wherein transverse compression of the transverse compression deformable body is in a direction perpendicular to the longitudinal axis of the device.

15. The device according to claim 1, wherein the expanding elements attaching to the wall of a vessel are formed in a hooked shape.

* * * * *